United States Patent [19]

Thies et al.

[11] 4,141,988
[45] Feb. 27, 1979

[54] 2,9-DIOXATRICYCLO[4,3,1,0$^{3,7}$]DECANE DERIVATIVES, PROCESSES FOR THEIR PREPARATION AND PHARMACEUTICAL COMPOSITIONS THEREOF

[75] Inventors: Peter W. Thies; Samuel David, both of Hannover, Fed. Rep. of Germany; Hartmut Hauth, Riehen; Dietmar Roemer, Allschwil, both of Switzerland

[73] Assignee: Kali-Chemie Pharma GmbH, Hannover, Fed. Rep. of Germany

[21] Appl. No.: 874,626

[22] Filed: Feb. 2, 1978

[30] Foreign Application Priority Data

Feb. 4, 1977 [DE] Fed. Rep. of Germany ....... 2704621

[51] Int. Cl.$^2$ ................... A61K 31/335; C07D 319/08
[52] U.S. Cl. ................................ 424/278; 260/340.3
[58] Field of Search ....................... 260/340.3; 424/278

[56] References Cited

U.S. PATENT DOCUMENTS

| | | | |
|---|---|---|---|
| 3,917,651 | 11/1975 | Thies ................................ | 260/340.3 |
| 4,016,176 | 4/1977 | Thies ................................ | 260/340.3 |

*Primary Examiner*—Ethel G. Love
*Attorney, Agent, or Firm*—Richard L. Schwaab

[57] ABSTRACT

4-amino-3-methyl-2,9-dioxatricyclo[4,3,1,0$^{3,7}$]decane derivatives are disclosed which exhibit analgesic properties, and which have the formula (I)

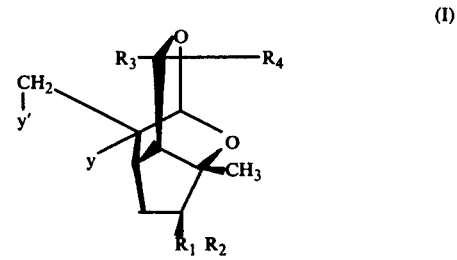

(I)

wherein
  one of $R_1$ and $R_2$ represents hydrogen and the other represents an amino group which is substituted by an arylalkyl group or an arylalkenyl group,
  one of $R_3$ and $R_4$ represents hydrogen and the other represents alkoxy, and
  y and y' each represent hydrogen or jointly form a bond, and pharmaceutically acceptable acid addition salts thereof, as well as pharmaceutical formulations thereof.

25 Claims, No Drawings

2,9-DIOXATRICYCLO[4,3,1,0³,⁷]DECANE DERIVATIVES, PROCESSES FOR THEIR PREPARATION AND PHARMACEUTICAL COMPOSITIONS THEREOF

BACKGROUND OF THE INVENTION

The invention relates to 4-amino-3-methyl-2,9-dioxatricyclo[4,3,1,0$^{3,7}$]decane derivatives and processes for their preparation and pharmaceutical compositions thereof.

The German Offenlegungsschrifts Nos. 1,961,433, 2,027,890, 2,129,507, and 2,306,118 and the corresponding U.S. Pat. Nos. 3,812,154 and 3,917,651 disclose 2,9-dioxatricyclo[4,3,1,0$^{3,7}$]decanes which possess central nervous system depressing, narcotic, neuroleptica-like and vasodilative activities. The German Offenlegungsschrift No. 2,547,205 discloses 2,9-dioxatricyclo[4,3,1,0$^{3,7}$]decanes which possess analgesic and sedative properties.

SUMMARY OF THE INVENTION

It is an object of the present invention to provide pharmacologically active 2,9-dioxatricyclo[4,3,1,0$^{3,7}$]-decane derivatives which exhibit strong analgesic activities, and are low in toxicity and in side effects.

It is a special object of the present invention to provide such analgesically active 2,9-dioxatricyclo[4,3,1,0$^{3,7}$]decane derivatives which exhibit analgesic properties which are similar to that of morphine, yet without addiction forming properties or undesirable side effects on the gastrointestinal tract, in particular the intestinal motility.

It is a further object of the present invention to provide pharmaceutical solid or liquid formulations containing 4-amino-3-methyl-2,9-dioxatricyclo[4,3,1,0$^{3,7}$]-decane derivatives.

It is a further object of the present invention to provide a method for the treatment or prevention of pains.

It is still a further object of the present invention to provide stereoselective processes for preparing primary and secondary 4-amino-3-methyl-2,9-dioxatricyclo[4,3,1,0$^{3,7}$]decane derivatives, especially processes which provide for obtaining such compounds in good yields.

In order to accomplish the foregoing objects according to the present invention, there are provided pharmacologically active 4-amino-3-methyl-2,9-dioxatricyclo[4,3,1,0$^{3,7}$]decane derivatives of the formula (I)

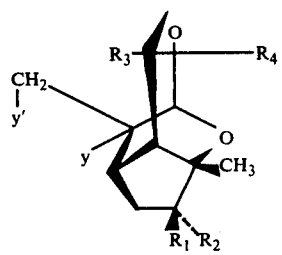

(I)

wherein
one of $R_1$ and $R_2$ represents hydrogen and the other represents an amino group which is substituted by an arylalkyl group or an arylalkenyl group,
one of $R_3$ and $R_4$ represents hydrogen and the other represents alkoxy, and
y and y' each represent hydrogen or jointly form a bond, and pharmaceutically acceptable acid addition salts thereof.

Surprisingly it has been found that by replacing the oxygen containing substituent in the 4-position of known 3-methyl-2,9-dioxatricyclo[4,3,1,0$^{3,7}$]decane derivatives by an amino group which is substituted by an arylalkyl- or an arylalkenyl group, compounds which exhibit an improved analgesic activity and are low in undesirable side effects are obtained.

The substituted amino group in the 4-position of the compounds of formula I preferably is a group having the formula IX

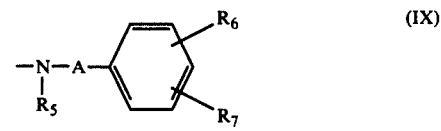

(IX)

wherein
$R_5$ represents hydrogen, alkyl containing 1 to 6 carbon atoms, or an alkenyl group containing 2 to 6 carbon atoms,
A represents alkylene containing 2 to 4 carbon atoms, or alkenylene containing 2 or 4 carbon atoms,
$R_6$ represents hydrogen, alkyl containing 1 to 4 carbon atoms, alkoxy containing 1 to 3 carbon atoms, halogen, or hydroxy, and
$R_7$ represents hydrogen, alkyl containing 1 to 4 carbon atoms, alkoxy containing 1 to 3 carbon atoms, halogen, or hydroxy.

Within the above formula IX, $R_5$ preferably is hydrogen. If $R_5$ represents alkyl, it preferably contains 1 to 4 carbon atoms and most preferably is methyl, if $R_5$ represents alkenyl, it preferably contains 3–4 carbon atoms and most preferably represents allyl.

If A represents alkylene, it most preferably is ethylene, if A represents alkenylene, it preferably is allylene.

If the substituents in the phenyl ring represent alkyl- or alkoxy groups, these preferably are methyl or methoxy. If the substituents in the phenyl group are halogens, these are chlorine, fluorine or bromine, preferably chlorine which most preferably is in the 2-position.

The substituted amino group in the 4-position of the 2,9-dioxatricyclo[4,3,1,0$^{3,7}$]decane cyclus preferably is in the 4 α-position. Most preferably this substituted amino group is 2-chlorophenethylamino.

The substituent in the 10-position of the 2,9-dioxatricyclo[4,3,1,0$^{3,7}$]decane cyclus preferably is methyl which preferably is in the 10 β-position.

The alkoxy substituent in the 8-position of the 2,9-dioxatricyclo[4,3,1,0$^{3,7}$]decane cyclus preferably contains 1 to 4 carbon atoms and most preferably is methoxy.

According to the present invention, there are further provided processes for preparing the compounds of formula (I) and of intermediates which are useful for their production.

For example a compound of formula V

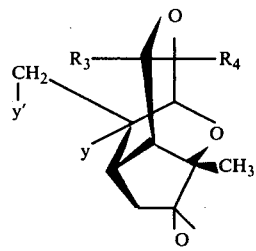

wherein $R_3$, $R_4$, y and y' are as defined in formula I is steroselectively transformed into one of the epimeric 4 α- and 4 β-amino compounds of formula IIIa or IIIb

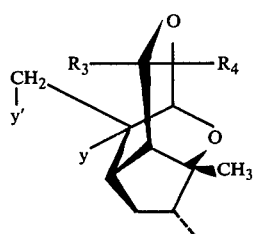

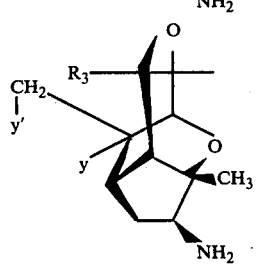

wherein $R_3$, $R_4$, y and y' are as defined in formula I and then the amino group is further substituted, or the compound of V is reacted with an aralkylamine under reducing conditions to form the corresponding 4 α-aralkylamino-compounds.

According to the present invention, there are further provided pharmaceutical compositions comprising the above described compounds of formula I or their pharmaceutically acceptable salts, and optionally an inert diluent.

Further objects, features and advantages of the present invention will become apparent from the detailed description of the invention which follows.

DETAILED DESCRIPTION OF THE INVENTION

The new compounds of formula I according to this invention and their pharmaceutically acceptable salts exhibit valuable pharmacological properties and therefore are useful in medical treatment. In particular, they are useful as analgesics, since they exhibit analgesic activities in animals as is indicated in standard tests, e.g., they inhibit the pain which is induced by means of bradykinin in rats upon s.c. administration of from 1 to 100 mg/kg body weight.

The pharmacological properties of the compounds according to the present invention will be further explained using the 4 α-(o-chlorophenethylamino)-3,10-dimethyl-8-methoxy-2,9-dioxatricyclo[4,3,1,0$^{3,7}$]decane hydrochloride (formula Xd, test substance No. 32-527) as an example.

The test substance No. 32-527 exhibits analgesic activities in mice, rats and rhesus monkeys upon enteral and parenteral administration. This analgesic activity is of about the same order as that of morphine. For example, the MED of both, the test substance 32-527 and morphine, is 0,56 mg/kg in the so-called step-irritation test in the rhesus monkey upon s.c. administration. Upon s.c. administration, the $ED_{50}$ of the two substances for inhibiting the bradykinin induced pain in rats are as follows:

test substance No. 32-527 < 5,6 mg/kg and morphine 3,6 mg/kg. Contrary to morphine in the self-administration test with the test substance No. 32-527 practically no addiction syndroms are observed in the rhesus monkey.

In tests evaluating the acute toxicity, the test substance No. 32-527 exhibits a similarly low toxicity as that of propoxyphene or profadol. Contrary to morphine, the test substance No. 32-527 does not inhibit the intestinal motility in mice upon oral administration of up to 100 mg/kg (intestinal motility inhibiting $ED_{50}$ of morphine is 39 mg/kg p.o.).

For the above mentioned therapeutical uses of the 4-amino-3-methyl-2,9-dioxatricyclo[4,3,1,0$^{3,7}$]decanes according to the present invention, the administered doses can vary considerably depending on the type of the compound, the animal, the mode of administration, the treated condition, and the therapy which is desired. Usually, satisfactory results are obtained with dosages between about 0.3 and 60 mg/kg body weight. These dosages can be administered enterally, preferably orally, or parenterally. For example, daily oral dosages for larger mammals can be chosen between about 10 and 100 mg, conveniently administered in 2 to 4 divided doses or in sustained release form.

Since the compounds according to the present invention possess a novel chemical structure and an analgesic activity which is similar to that of morphine, yet do not exhibit any addiction forming properties in long term tests or any undesirable effect on the gastro-intestinal tract, they provide highly active, less dangerous analgesics for which a world wide need exists.

According to a further feature of the invention, there are provided pharmaceutical compositions containing at least one of the compounds of formula (I) or their pharmaceutically acceptable salts. The compositions may take the form of solid or liquid formulations for enteral, preferably oral, or for parenteral administration. Thus, the formulations may be in the form of capsules, tablets, coated tablets, suppositories, emulsions or solutions. These formulations may comprise conventional pharmaceutical carriers, e.g., solids, such as starch, lactose, mannit, polyvinyl pyrrolidone or liquids such as sterile water, pharmaceutically acceptable alcohols or fatty oils, and may further comprise pharmaceutical adjuvants, e.g., binders or lubricants for tabletting, stabilizing, flavoring or emulsifying agents.

The novel compounds are prepared by highly stereoselective processes as follows:

Compounds of formula (Ia)

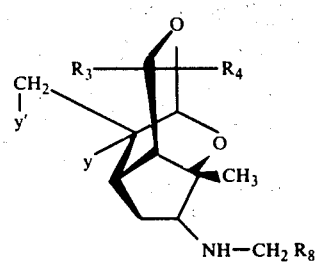

wherein
R$_8$ represents alkylaryl, alkenylaryl or aryl,
one of R$_3$ and R$_4$ represents hydrogen and the other represents alkoxy, and
y and y' each represent hydrogen or jointly form a bond, are prepared by reducing a compound of the formula II

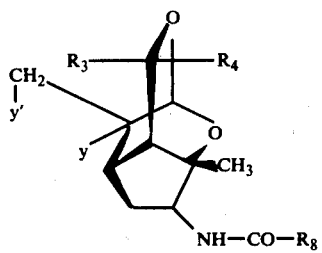

wherein
R$_3$, R$_4$, R$_8$, y and y' are as defined above.

The reduction of the carboxylic acid amides of formula II is suitably effected in a solvent by means of a metal hydride, preferably a metal hydride complex. Suitable metal hydrides are aluminiumhydride complexes such as diethyl aluminium hydride, lithium aluminium hydride, diisobutyl aluminium hydride, and diborane, and suitable solvents are open chained or cyclic ethers such as diethyl, ether, tetrahydrofurane, dioxane or diglyme.

The reaction may be carried out at a temperature of between about room temperature and about 100° C.

The intermediate compounds of formula II are obtained by reacting a compound of the formula III

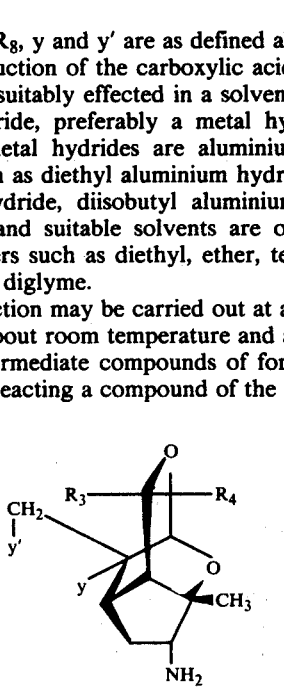

wherein
R$_3$, R$_4$, y and y' are as defined in formula II with an active derivative of an acid R$_8$-COOH wherein R$_8$ is as defined in formula II. Suitable active acid derivatives are acid halides, especially acid chlorides.

In order to obtain the 4 α-amino epimer of the starting material of formula III, the compound of formula V is reacted with a hydroxylammonium salt, preferably hydroxylammonium chloride to form an oxime-compound of formula IV

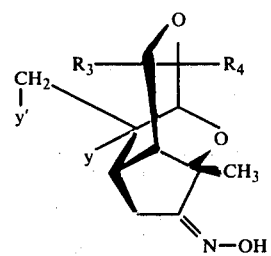

wherein
R$_3$, R$_4$, y and y' are as defined in formula III. This oxime of formula IV is then stereoselectively reduced to the 4 α-amine compound of formula IIIa. This reduction is preferably effected by means of hydrogen in the presence of Raney-nickel, or by means of metal hydrides.

In order to obtain the 4 β-amino epimer of the starting material of formula III, the compound of formula V is stereoselectively reduced to the 4 α-hydroxy compound of formula VIII

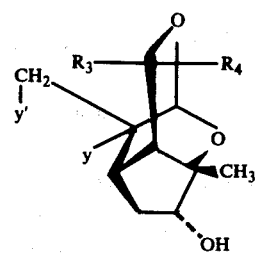

wherein
R$_3$, R$_4$, y and y' are as defined in formula III, which then is esterified with an active derivative of sulfonic acid R$_9$OH wherein R$_9$ is as defined in formula VII to form a compound of formula VII

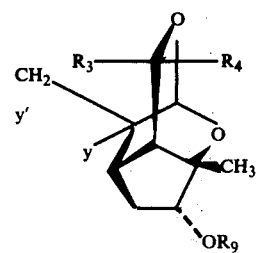

wherein
R$_3$, R$_4$, y and y' are as defined in formula III and R$_9$ is tosyl or mesyl. The stereoselective reduction of the decanone compound of formula V is suitably effected by means of a metal hydride, preferably an aluminium hydride complex, for example, according to the method which is described in the German Offenlegungsschrift No. 23 06 118, the disclosure of which is hereby incorporated by reference.

The compound of formula VII is then reacted with an alkali azide, preferably sodium azide to form a 4 β-azido compound of formula VI

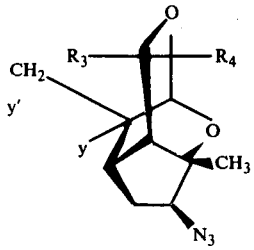

(VI)

wherein $R_3$, $R_4$, y and y' are as defined in formula III, and which subsequently is reduced into a 4 β-amino-compound of the formula IIIb.

The reaction of the compound of formula VII with an alkali azide, which comprises an inversion of the position of the substituent in the 4-position can be effected in a conventional manner, e.g., by reacting the compound of formula VII with the alkali azide in an aprotic solvent, preferably dimethylformamide or hexamethyl phosphoric acid amide.

The reduction of the azide formula VI is suitably effected by means of hydrogen or hydrazine in the presence of Raney-nickel, or by means of a metal hydride complex.

If a double bond is present in the 10-position of the decanone starting material of formula V, this double bond is not effected by a reduction using a metal hydride as a reducing agent. In the case where a reduction is effected by means of hydrogen or hydrazine in the presence of Raney-nickel, the hydrogen uptake can be adjusted by changing the pH of the reaction medium in such a way, that the double bond is hydrogenated in an alkaline reaction medium, or that it remains uneffected in an acidic reaction medium.

A compound of formula Ic

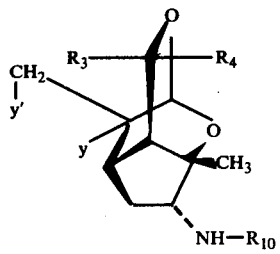

(Ic)

wherein $R_3$, $R_4$, y and y' are as defined in formula V and $R_{10}$ represents an aralkyl group, can be prepared by reacting a compound of formula V with an amine of $R_{10}$—$NH_2$ wherein $R_{10}$ is as defined in formula Ic under reducing conditions. The reductive amination can be effected in the presence of a metal hydride complex, such as sodium cyanoboron hydride and a solvent. The reductive amination can also be effected in the presence of formic acid and a solvent. In the latter case the reductive amination is suitably effected at an elevated temperature, e.g., a temperature of between about 120° and about 180° C.

A compound of the formula Ib

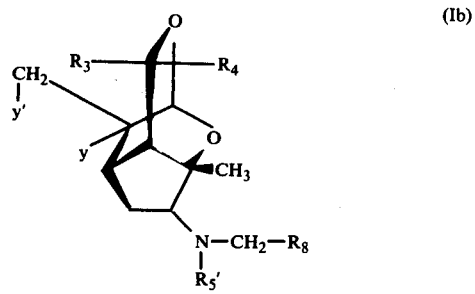

(Ib)

wherein $R_3$, $R_4$, $R_8$, y and y' are as defined in formula Ia and $R_5'$, represents alkyl or alkenyl, is prepared by alkylating a compound of formula Ia in a conventional manner.

Instead of reacting an amino-compound of formula III with an active derivative of an acid of the formula $R_8$-COOH and reducing the intermediate acid amide of formula II to prepare a compound of formula Ia, a compound of formula Ia may be prepared by reacting an amine of formula III with an aldehyde of formula $R_8$-CHO under reducing conditions.

The reaction preferably is carried out in a solvent, preferably at elevated temperature. Suitable solvents are the above mentioned open chained or cyclic ethers, preferably tetrahydrofurane. The reducing agent is a metall hydride, preferably sodium borohydride.

This alternative route for preparing a compound of formula Ia may be characterised as a subvariant to variant 1 and variant 3. Example 5 below, which describes the preparation of the cinnamylamino-derivative, may serve as an example for this alternative general route.

The compounds according to the present invention are prepared starting from the decanone compounds of formula V according to 3 different reaction sequences, two of which lead to 4 α-amino compounds and one of which leads to 4 β-amino compounds. These reaction sequences are further explained in the general reaction scheme below, which summarizes the reactions which take place in preparing the compounds as described in example 1 below.

In this reaction scheme, the tricyclic structure is fully drawn only in the starting material Vd and in the two diastereoisomeric end products Id and Ie. For the intermediates, only the substituent in the 4-position of the tricyclic system is fully drawn, whereas the remaining portion of the molecule is indicated by a dotted line.

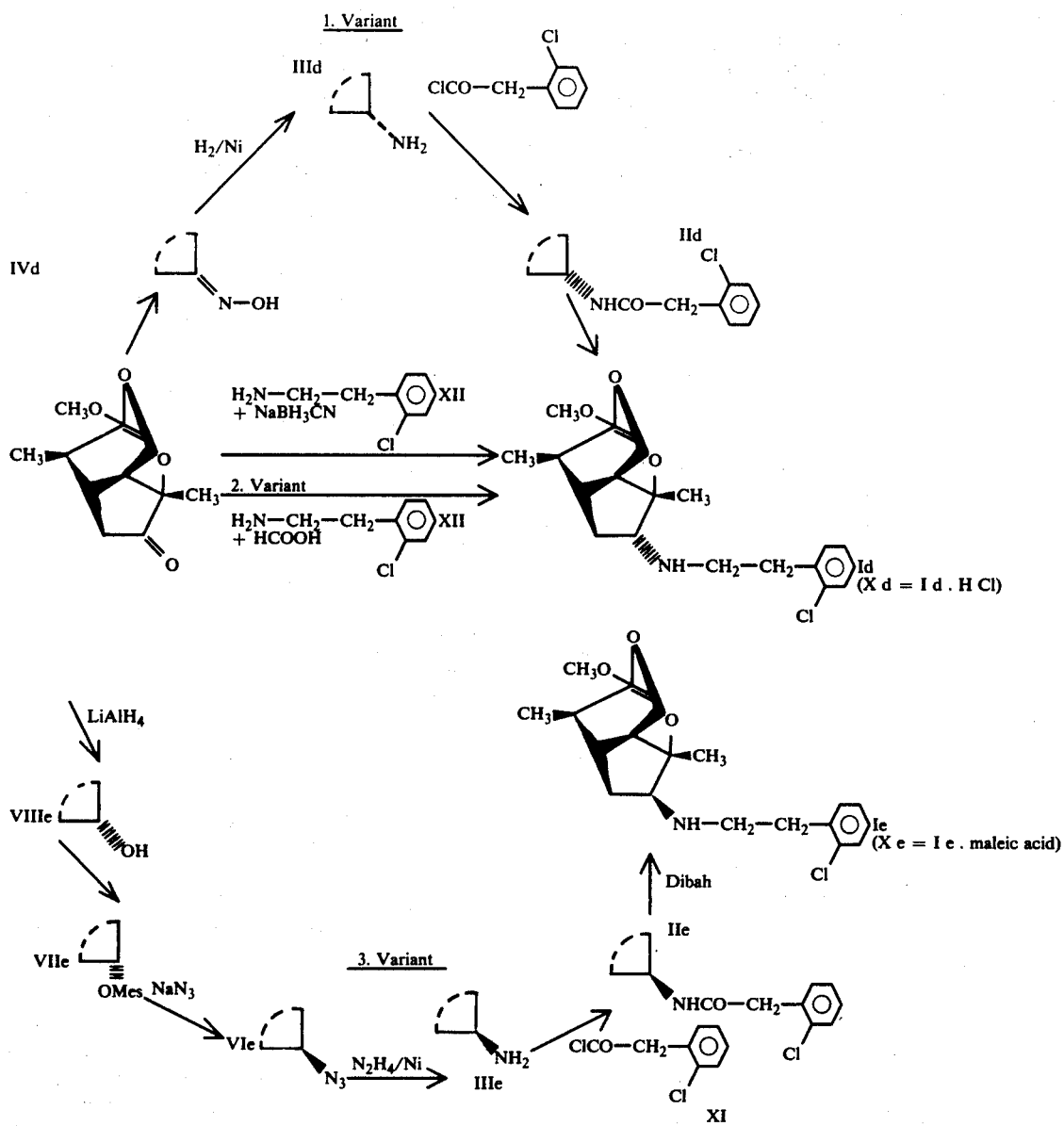

The present invention is, of course, not limited to the reactants and/or reaction condition which are shown in the general reaction scheme which is given for exemplifying purposes only.

According to the first variant of the reaction sequences the decanone (Vd) is first transformed into the oxime (IVd), which then is stereoselectively reduced to 4 α-amine (IIId) by means of hydrogen in the presence of Raney-nickel or by means of metal hydrides. The 4 α-amine is then reacted with o-chlorophenyl acetic acid chloride (XI) to form the carboxylic acid amide (IId), which is then reduced to the desired 4 α-(o-chlorophenethylamino) compound (Id).

The second variant of the reaction sequences represents a reductive amination of the decanone (Vd) by means of o-chlorophenethyl amine (XII). The amination takes place either in the presence of a metal hydride complex, e.g., sodium cyanoboron hydride (variant 2 a) or in the presence of formic acid (variant 2b).

Both, variant 2a and variant 2b yield directly the final 4 α-amino product (Id).

According to the third variant of the reaction sequences, the decanone Vd is first stereoselectively reduced to the 4 α-compound (VIIIe) which is then transformed into the mesylate (VIIe) or the corresponding tosylate, which by means of an azide is transformed into the 4 β-azido compound (VIe).

The azide (VIe) is then reduced into the 4 β-amine IIIe by means of hydrogen or hydrazine in the presence of Raney-nickel or by means of a metal hydride complex. The 4 β-amine is then transformed in the 4 β-carboxylic acid amide (IIe) and the latter is reduced into the final 4 β-amino-product Ie in the same manner as the corresponding 4 α-compounds in the first variant.

The starting materials of formula V and their preparation is described in the U.S. Pat. No. 3,917,651 the disclosures of which is hereby incorporated by reference.

The 10-methyl compounds of formula V are obtained by hydrogenating the 10,11-double bond in the 10-methylene compounds of formula V in known manners. The hydrogenation product is a mixture of the epimeric 10 α-methyl and 10 β-methyl compounds which can be seperated by conventional methods.

The compounds of formula I can be recovered in free form or in form of a salt. A salt form can easily be transferred into the free form and vice versa in conventional manners. Acid addition salts of compounds of formula (I) can be formed with mineral acids such as, hydrochloric, hydrobromic, or sulfuric acid or with organic acids such as maleic or tartaric acid.

EXAMPLE 1

Preparation of 4α-[2-(2-chlorophenyl)ethylamino]-3,10-dimethyl-8-methoxy-2,9-dioxatricyclo]4,3,1,0$^{3,7}$]-decane-hydrochloride (Xa) from 3,10-dimethyl-8-methoxy-2,9-dioxatricyclo [4,3,1,0$^{3,7}$]decane-4-one (Vd).

Process Variant 1

(a) Preparation of 3,10-dimethyl-8-methoxy-2,9-dioxatricyclo]4,3,1,0$^{3,7}$]decane-4-oxime (IVd) from (Vd).

A solution of 1.75 g hydroxylammonium chloride is added to 5 g of (Vd) in 70 ml pyridine and is stirred at room temperature for 2 hours. Then the mixture is repeatedly evaporated to dryness under addition of ethanol and subsequently is poured into ice water. The resulting mixture is extracted with ether. The combined organic phases are dried over sodium sulfate, filtered and evaporated. The substance is crystallized from ether/n-hexane.

Yield: 4.7 g of (IVd) (= about 89% of the theoretical amount)

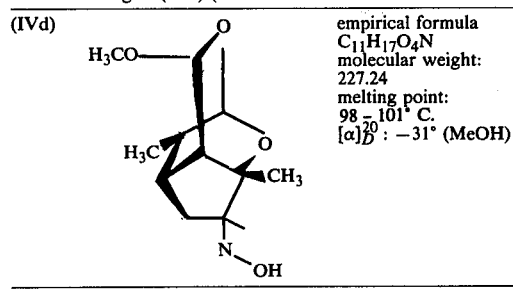

(IVd)
empirical formula C$_{11}$H$_{17}$O$_4$N
molecular weight: 227.24
melting point: 98 – 101° C.
[α]$_D^{20}$: −31° (MeOH)

(b) Preparation of 4α-amino-3,10-dimethyl-8-methoxy-2,9-dioxatricyclo]4,3,1,0$^{3,7}$]decane (IIId) from (IVd). Raney-nickel is added to a solution of 5 g of (IVd) in 150 ml methanol and the mixture is hydrogenated at room temperature under normal pressure. Upon completion of the hydrogen uptake, the catalyst is filtered off and the solution is evaporated to dryness under vacuum.

Yield: 4.1 g of (IIId) (= about 87% of the theoretical amount).

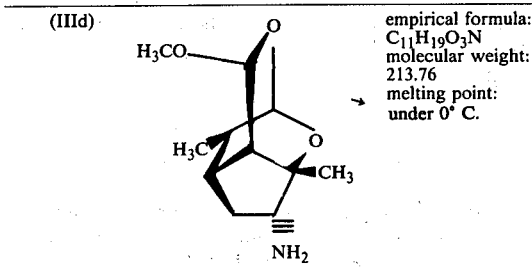

(IIId)
empirical formula: C$_{11}$H$_{19}$O$_3$N
molecular weight: 213.76
melting point: under 0° C.

(c) Preparation of 4 α-[2-(2-chlorophenyl)acetamido]-3,10-dimethyl-8-methoxy-2,9-dioxatricyclo[4,3,1,0$^{3,7}$]decane (IId) from (IIId).

35.3 g (0.16 mol) of (IIId) are dissolved in 150 ml toluene and 10 ml of pyridine are added. This mixture is added dropwise to a solution of 32,13 g (0,17 Mol) 2-chlorophenyl acetic acid chloride (XI) in 75 ml toluene. The solution is then being stirred for one hour at room temperature and subsequently is repeatedly evaporated to dryness under addition of toluene. The residue is dissolved in methylene chloride and the solution is then shaken one time with water. After drying the organic phase, the solvent is evaporated under vacuum. Yield: 47.4 g of the raw product (=78% of the theoretical amount).

After purifying the raw product over aluminium oxide using a CH$_2$Cl$_2$/n-hexane mixture as a solvent, 33.7 g (=55% of the theoretical amount) of the crystalline product are obtained.

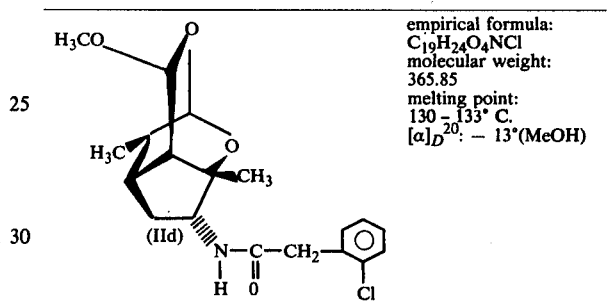

empirical formula: C$_{19}$H$_{24}$O$_4$NCl
molecular weight: 365.85
melting point: 130 – 133° C.
[α]$_D^{20}$: − 13°(MeOH)

(d) Preparation of 4α-[2-(2-chlorophenyl)ethylamino]-3,10-dimethyl-8-methoxy-2,9-dioxatricyclo[4,3,1,0$^{3,7}$]decane (Id) from (IId).

To a solution of 1 g of (IId) in 30 ml of tetradrofurane (dry) a solution of 1 ml of diethylaluminiumhydride in 5 ml of tetrahydrofurane is added dropwise at a temperature of 0° C. and the solution is then stirred for two hours at room temperature. Subsequently a solution of 1–2% water in methanol is carefully added and then water is added. After adding a NaHCO$_3$-solution up to the alkaline reaction point, the mixture is extracted with methylene chloride. Upon drying and filtering of the organic phase, the solvent is evaporated under vacuum. 0.9 g of the raw product are obtained.

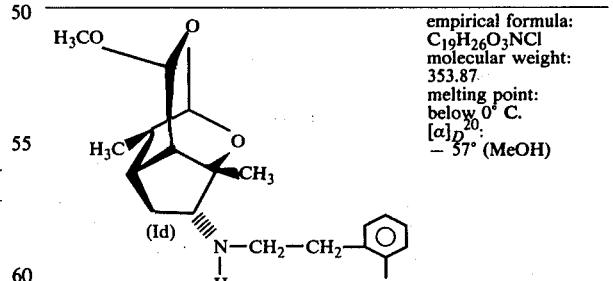

empirical formula: C$_{19}$H$_{26}$O$_3$NCl
molecular weight: 353.87
melting point: below 0° C.
[α]$_D^{20}$: − 57° (MeOH)

(e) Preparation of 4α-[2-(2-chlorophenyl)ethylamino]-3,10-dimethyl-8-methoxy-2,9-dioxatricyclo[4,3,1,0$^{3,7}$]decane hydrochloride (Xd) from (Xd).

A solution of 0.9 g of the raw amine (Id) in 10 ml ether is added dropwise, while stirring, to 10 ml of a 10% aqueous hydrochloric acid. Stirring is continued for another 30 minutes and the precipitate is filtered off. Recrystallization from methanol/ether yields 0.9 g of (Xd) (=85% of the theoretical amount).

with ether. The combined organic phases are dried, filtered and the solvent evaporated.

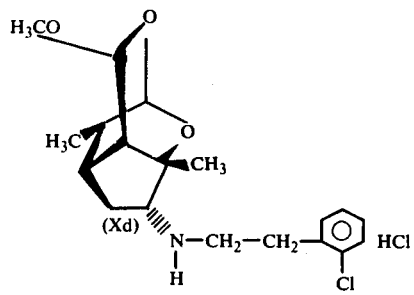

empirical formula: C$_{19}$H$_{27}$O$_3$NCl$_2$
molecular weight: 389.37
melting point: 231 – 233° C.
$[\alpha]_D^{20}$: – 17.2°

Process Variant 2a

Preparation of 4α-[2-(2-chlorophenyl) ethylamino]-3,10-dimethyl-8-methoxy-2,9-dioxatricyclo[4,3,1,0$^{3,7}$]-decane hydrochloride (Xd) directly from 3,10-dimethyl-8-methoxy-2,9-dioxatricyclo[4,3,1,0$^{3,7}$]decane-4-one (Vd).

To a solution of (Vd) in 500 ml of absolute ethanol 2-(2-chlorophenyl)-ethylamine (XII) and 1 ml of concentrated HCl are added. After stirring for one hour at room temperature, 50 g of dry MgSO$_4$ are added and the solution is stirred for another two hours. Subsequently, 10 g of sodium cyanoboronhydride are added in small portions, distributed over a period of several days. Thereafter, part of the ethanol is destilled off and, after adding 300 ml of water, the solution is extracted with ether. The purified organic phase is slightly concentrated and then a 10% HCl-solution is added. The resulting precipitate is filtered off and washed with ether. Yield: 26 g (=about 43% of the theoretical amount).

Process Variant 2b

Preparation of 4 α-[2-(2-chlorophenyl)ethylamino]-3,10-dimethyl-8-methoxy-2,9-dioxatricyclo[4,3,1,0$^{3,7}$]-decane hydrochloride (Xd) directly from 3,10-dimethyl-8-methoxy-2,9-dioxatricyclo[4,3,1,0$^{3,7}$]decane-4-one (Vd). 9 ml of formic acid are added to a mixture of 30 g of (Vd) and 50 g of 2-(2-chlorophenyl)ethylamine (XII) and the mixture is heated to 150° C. while stirring. After six hours the solution is cooled and 100 ml of water and 50 ml of ether are added. Thereafter 100 ml semi-concentrated hydrochloric acid are added. The precipitate is filtered off and is recrystallized from methanol/ether. Yield: 42 g of raw product (83%);32 g = 63% of the theoretical amount (after recrystillization).

Process Variant 3

Preparation of 4β-[2-(2-chlorophenyl)ethylamino-3,10-dimethyl-8-methoxy-2,9-dioxatricyclo[4,3,1,0$^{3,7}$]decanmaleate (Ie) from 3,10-dimethyl-8-methoxy-2,9-dioxatricyclo[4,3,1,0$^{3,7}$]decane-4-one (Vd).

(a) Preparation of 4α-hydroxy-3,10-dimethyl-8-methoxy-2,9-dioxatricyclo[4,3,1,0$^{3,7}$]decane (VIIIe) from (Vd).

7 g of Vd are dissolved in 100 ml of absolute ether and the solution is added dropwise to a slurry of 1.4 g LiAlH$_4$ in 50 ml ether, which is stirred for 30 minutes at room temperature. Subsequently moist ether and then water are added, and the aqueous phase is extracted Yield 5.9 g of (VIIIe).

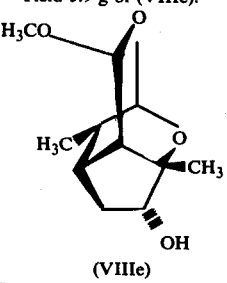

(VIIIe)

empirical formula: C$_{11}$H$_{18}$O$_4$
molecular weight: 214.76
melting point: > 0° C.
$[\alpha]_D^{20}$: – 65° (MeOH)

(b) Preparation of 4α-methanesulfonate-3,10-dimethyl-8-methoxy-2,9-dioxatricyclo [4,3,1,0$^{3,7}$]decane (VIIe) from (VIIIe).

1 g of (VIIIe) is dissolved in 5 ml of pyridine. A suspension of 0.7 ml methanesulfonylchloride in 3 ml pyridine is added dropwise under cooling with ice. Thereafter the solution is kept under refrigeration over night. The solution is then repeatedly evaporated to drieness under addition of ethanol. The residue is dissolved in ether and shaken with water. The organic phase was dried, filtered and the solvent evaporated.

Yield: 0.9 g

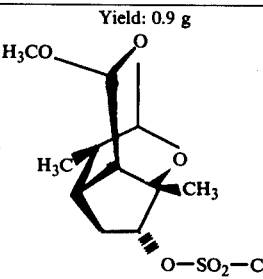

(VIIe)

empirical formula: C$_{12}$H$_{20}$SO$_6$
molecular weight: 292.35
melting point: 102 – 103° C.
$[\alpha]_D^{20}$: –32.7° (MeOH)

(c) Preparation of 4β-azido-3,10-dimethyl-8-methoxy-2,9-dioxatricyclo [4,3,1,0$^{3,7}$]decane (VIe) from (VIIe).

2.5 g of sodium azide are added to 1 g of (VIIe) in 15 ml of dimethylformamide and the mixture is heated to 150° C. while stirring. After 6 hours, the solvent is evaporated and the residue is dissolved in ether and washed with water. The organic phase is dried over sodium sulfate, filtered and the solvent is evaporated under vacuum. Yield: 0.7 g (85% of the theoretical amount).

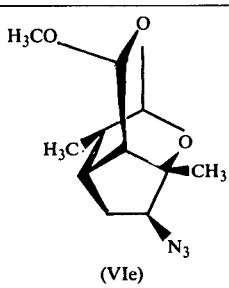

(VIe)

empirical formula:
C₁₁H₁₇N₃O₃
molecular weight:
239.27
melting point:
> 0° C.
[α]$_D^{20}$:
+27° (MeOH)

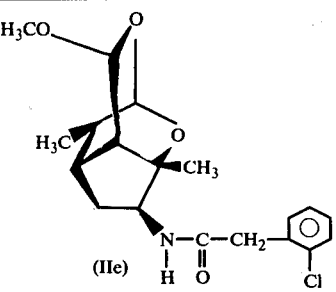

(IIe)

empirical formula:
C₁₉H₂₄O₄NCl
molecular weight:
365.85
melting point:
202 – 4° C.
[α]$_D^{20}$:
−21.2° (MeOH)

(d) Preparation of 4β-amino-3,10-dimethyl-8-methoxy-2,9-dioxatricyclo[4,3,1,0³,⁷]decane (IIIe) from (VIe).

2 ml of a 80% solution of hydrazine hydrate are added to 1 g of (VIe) in 10 ml of methanol p.a. A small amount of Raney-nickel is added to this solution. Hereby a gas formation starts spontaneously and lasts for about 30 minutes. Subsequently the solution is filtered, and the residue is washed with methanol. The combined phases are evaporated under vacuum. After the product has been purified over silica gel, using an n-hexane/ether mixture as a solvent, 0.8 g of (IIIe) (90% of the theoretical amount) are obtained.

(f) Preparation of 4 β-[N-(o-chlorophenethyl)amino]-3,10-dimethyl-8-methoxy-2,9-dioxatricyclo [4,3,1,0³,⁷]decane (Ie) from (IIe).

27 ml of diisobutylaluminium hydride (70% in toluene) are added to a solution of 9.7 g of the raw crystals of (IIe) in 100 ml benzene. The mixture is stirred for one hour at room temperature under nitrogen atmosphere. Subsequently 5o ml of a 10% solution of methanol in benzene is added dropwise, followed by 50 ml of methanol. The solution is evaporated, the residue is dissolved in ether and shaken with water. The organic phase is dried and the solvent evaporated. Yield: 4.36 g (46% of the theoretical amount).

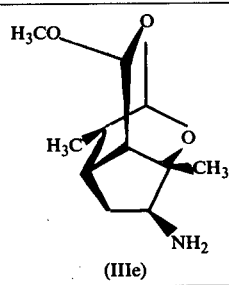

(IIIe)

empirical formula:
C₁₁H₁₉O₃N
molecular weight:
213.31
melting point:
> 0° C.
[α]$_D^{20}$:
−10.6° (MeOH)

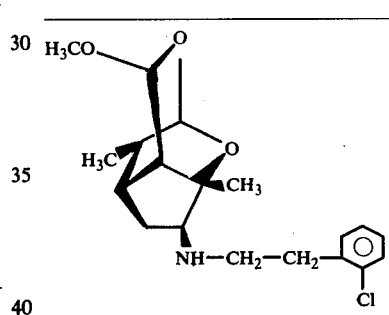

empirical formula:
C₁₉H₂₆O₃NCl
molecular weight:
353.87
melting point:
> 0° C.
[α]$_D^{20}$:
+24.8° (MeOH)

(e) Preparation of 4β[2-(o-chlorophenyl)acetamido]-3,10-dimethyl-8-methoxy-2,9-dioxatricyclo[4,3,1,0³,⁷]-decane (IIe) from (IIIe).

5 ml of pyridine are added to 7.8 g of (IIIe) in 50 ml benzene. Then a solution of 7.5 ml of 2-chlorophenylacetic acid chloride (XII) in 20 ml benzene is added dropwise at room temperature under nitrogen atmosphere. Subsequently the solution is repeatedly evaporated under addition of toluene. The residue is dissolved in methylene chloride, the solution is shaken with water and then dried, filtered and evaporated to dryness. Yield: 11.5 g of raw crystals (86.1% of the theoretical amount).

(g) Preparation of 4β-[N-(o-chlorophenethyl]amino-3,10-dimethyl-8-methoxy-2,9-dioxatricyclo[4,3,1,0³,⁷]-decane-maleate (Xe) from (Ie).

4.3 g of (Ie) are dissolved in 50 ml of ether. Within a period of 20 minutes, a solution of 1.5 g maleic acid in 20 ml of ether is added dropwise. The resulting precipitate is filtered and dried. Yield: 4.5 g (about 78% of the theoretical amount).

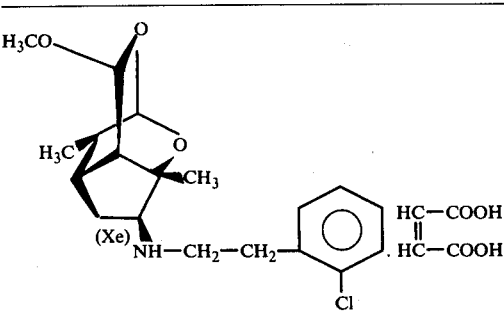

empirical formula:
C₂₃H₃₀O₇NCl
molecular weight:
469.94
melting point:
175 – 177° C.
[α]$_D^{20}$:
+22° (MeOH)

EXAMPLE 2

(a) Preparation of 4 α-[N-(o-chlorophenethyl)-N-methylamino]-3,10-dimethyl-8-methoxy-2,9-dioxatricyclo [4,3,1,0$^{3,7}$]decane (If) from (Id).

5 ml of a solution of 37% formaldehyde and a very small amount (spatula tip) of Raney-nickel are added to a solution of 5 g of (Id) in 100 ml of methanol, and the mixture is subsequently hydrogenated at room temperature under normal pressure. After the hydrogen uptake is completed, the catalyst is filtered off and the solution is concentrated and purified over Al$_2$O$_3$.

Yield: 4.1 g (about 79% of the theoretical amount).

2.5 ml of allyl bromide are added dropwise to a mixture of 8.79 g of (Id) and 9 g of K$_2$CO$_3$ in 30 ml dimethyl-foramide, at room temperature.

The mixture is then stirred for 30 minutes at room temperature and then stirred for six hours at 50° C. Thereafter, water, which is saturated with(NH$_4$)$_2$SO$_4$, is added, and then it is shaken with ether. The combined organic phases are dried over sodium sulfate, filtered and concentrated. After purifying the oily raw product (9.2 g) over aluminium oxide using an n-hexane/ether mixture as a solvent, 10.5 g (about 65% of the theoretical amount) were obtained.

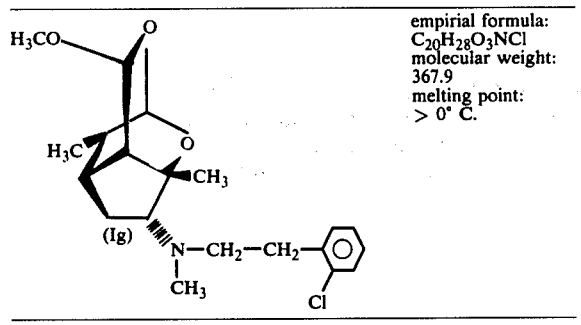

empirial formula:
C$_{20}$H$_{28}$O$_3$NCl
molecular weight:
367.9
melting point:
> 0° C.

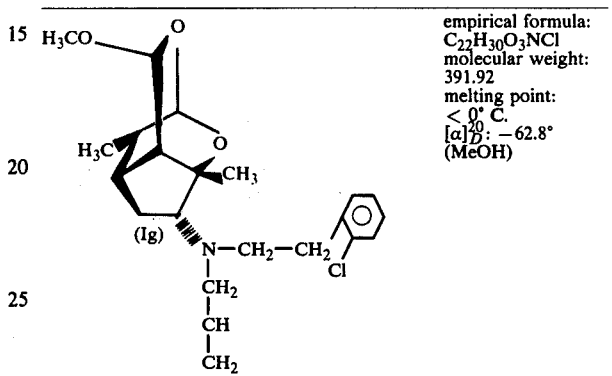

empirical formula:
C$_{22}$H$_{30}$O$_3$NCl
molecular weight:
391.92
melting point:
< 0° C.
[α]$_D^{20}$: −62.8°
(MeOH)

(b) Preparation of 4α-[N-(o-chlorophenethyl)-N-methylamino]-3,10-dimethyl-8-methoxy-2,9-dioxatricyclo [4,3,1,0$^{3,7}$]decane tartrate (Xf) from (I f).

1.5 g of tartaric acid are added to a solution of 2 g of 4α-[N-(o-chlorophenethyl)-N-methylamino]3,10-dimethyl-8-methoxy-2,9-dioxatrycyclo[4,3,1,0$^{3,7}$]decane in 20 ml of methanol and the solution is heated to 40°. The resulting oil is separated and triturated with ether.

Yield: 7 g (about 73% of the theoretical amount).

EXAMPLE 4

Preparation of 4 α-(3-phenylpropylamino)-3,10-dimethyl-8-methoxy-2,9-dioxatricyclo-[4,3,1,0$^{3,7}$]decane-hydrochloride (Xh) from 3,10-dimethyl-8-methoxy-2,9-dioxatricyclo[4,3,10$^{3,7}$]decane-4-one (Vd).

20 g of 3-phenylpropylamine and 3 ml of formic acid are added to 10g of (Vd) and the mixture is heated to 150° C. for 3½ hours while stirring. Subsequently the

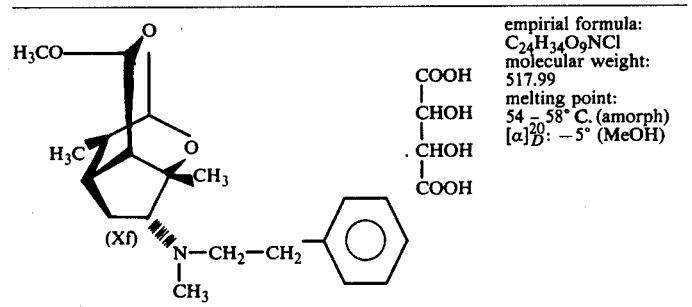

empirial formula:
C$_{24}$H$_{34}$O$_9$NCl
molecular weight:
517.99
melting point:
54 – 58° C. (amorph)
[α]$_D^{20}$: −5° (MeOH)

EXAMPLE 3

Preparation of 4α [N-(o-chlorophenethyl-N-allylamino]-3,10-dimethyl-8-methoxy-2,9-dioxatricyclo[4,3,1,0$^{3,7}$]decane (Ig) from 4 α-[N-(2o-chlorophenethyl)amino]-3,10-dimethyl-8-methoxy-2,9-dioxatricyclo[4,3,1,0$^{3,7}$]decane (Id).

solution is cooled and diluted with 50 ml ether. Thereafter 100 ml of a diluted hydrochloric acid solution are added and the resulting precipitate is filtered off and recrystallized from methanol/ether.

Yield: 7.64 g (about 44.1% of the theoretical amount).

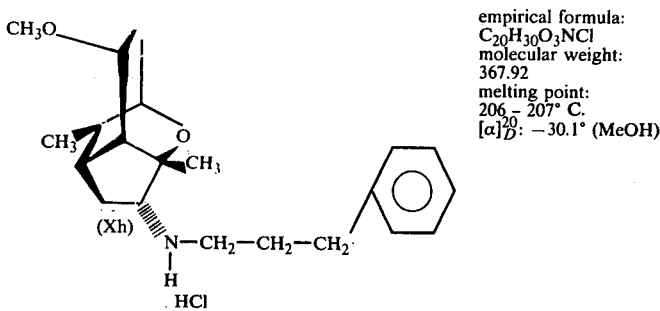

empirical formula:
$C_{20}H_{30}O_3NCl$
molecular weight:
367.92
melting point:
206 – 207° C.
$[\alpha]_D^{20}$: −30.1° (MeOH)

Analogous to Example 4, the following compounds are prepared:

4α-(4-phenylbutylamino)-3,10-dimethyl-8-methoxy-2,9-dioxatricyclo[4,3,1,0$^{3,7}$]decane-hydrochloride (Xi).

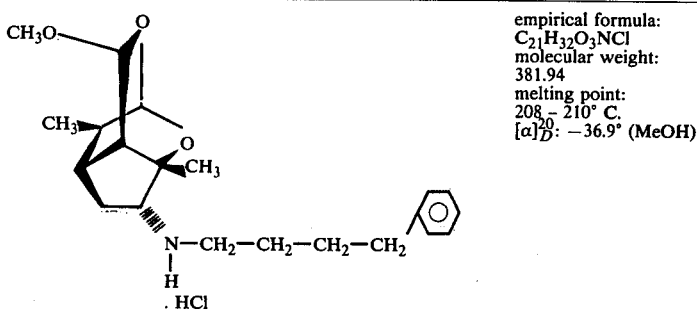

empirical formula:
$C_{21}H_{32}O_3NCl$
molecular weight:
381.94
melting point:
208 – 210° C.
$[\alpha]_D^{20}$: −36.9° (MeOH)

Yield: 8,7 g (about 48,4% of the theoretical amount).

4 α-[3-(2-chlorophenyl)propylamino]-3,10-dimethyl-8-methoxy-2,9-dioxatricyclo[4,3,1,0$^{3,7}$]decane-hydrochloride (Xj).

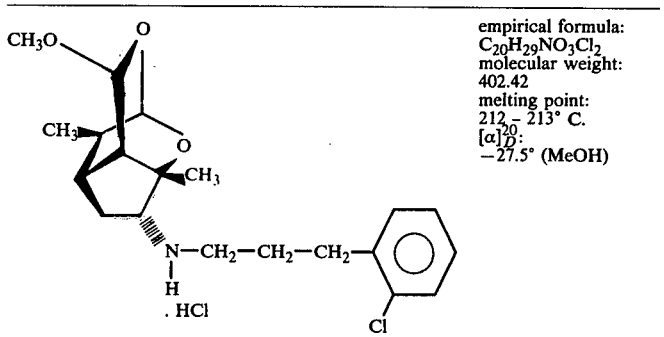

empirical formula:
$C_{20}H_{29}NO_3Cl_2$
molecular weight:
402.42
melting point:
212 – 213° C.
$[\alpha]_D^{20}$:
−27.5° (MeOH)

Yield: 1.83 g (about 61% of the theoretical amount).

EXAMPLE 5

Preparation of 4 α-(cinnamylamino)-3,10-dimethyl-8-methoxy-2,9-dioxatricyclo[4,3,1,0$^{3,7}$]decane-maleate(Xk) from 4 α-amino-3,10-dimethyl-8-methoxy-2,9-dioxatricyclo[4,3,1,0$^{3,7}$] decane (IIId).

6.2 g of cinnamaldehyde are added to a solution of 10 g (IIId) in 50 ml tetrahydrofurane and refluxed for three hours. Subsequently 20 ml of methanol and 1 g of NaBH$_4$ are added in small portions, the solution is evaporated under vacuum, mixed with 50 ml of water and extracted with ether. The combined organic phases are concentrated under vacuum and subsequently a solution of 4 g of maleic acid in 20 ml of ether is added dropwise. The resulting precipitate is filtered off, washed with ether and dried under vacuum.

Yield: 10.1 g of the maleinate (about 48.5% of the theoretical amount).

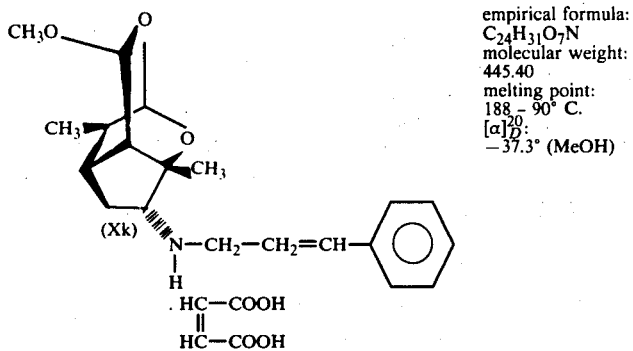

empirical formula:
$C_{24}H_{31}O_7N$
molecular weight:
445.40
melting point:
188°–90° C.
$[\alpha]_D^{20}$:
−37.3° (MeOH)

Analogous to the procedure described in Example 1, the following compounds are prepared 4 α- (o-chlorophenethylamino)-3methyl-8-methoxy-10-methylene-2,9-dioxatricyclo[4,3,1,0³,⁷]decane 4 β-(o-chlorophenethylamino)-3-methyl-8-methoxy-10-methylene-2,9-dioxatricyclo [4,3,1,0³,⁷]decane 4α-(o-methoxyphenethylamino)-3,10-dimethyl-8-methoxy-2,9-dioxatricyclo[4,3,1,0³,⁷]decane 4α-[2-(3,4-dimethoxyphenyl)ethylamino]-3,10-dimethyl-8-methoxy-2,9-dioxatricyclo [4,3,1,0³,⁷]decane 4 α-[2-(4-fluorophenyl)ethylamino]-3,10-dimethyl-8-methoxy-2,9-dioxatricyclo [4,3,1,0³,⁷]decane 4α-[2-(2-fluorophenyl)ethylamino]-3,10-dimethyl-8-methoxy-2,9-dioxatricyclo [4,3,1,0³,⁷]decane 4α-[2-(2-bromophenyl)ethylamino]-3,10-dimethyl-8-methoxy-2,9-dioxatricyclo [4,3,1,0³,⁷]decane.

EXAMPLE 6

CAPSULES FOR ORAL APPLICATION

| | |
|---|---|
| 4α-[2-(2-chlorophenyl)-ethylamino]-3,10-dimethyl-8-methoxy-2,9-dioxatricyclo[4,3,1,0³,⁷]decane-hydrochloride | 20 g |
| lactose | 60 g |
| starch | 18.5 g |
| magnesium stearate | 1.5 g |

The components are thoroughly mixed and the mixture is filled into gelatin capsules in portions of 100 mg per capsule.

EXAMPLE 7

One capsule, which is prepared according to Example 6, is administered to an adult person once a day for the treatment of pains.

What is claimed is:

1. A compound selected from the group of 2,9-dioxatricyclo [4,3,1,0³,⁷]decanes of the formula I

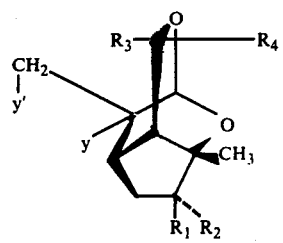

(I)

wherein one of $R_1$ and $R_2$ represents hydrogen and the other represents an amino group having the formula

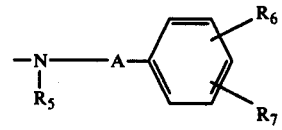

wherein $R_5$ represents hydrogen, alkyl containing 1 to 6 carbon atoms or an alkenyl group containing 2 to 6 carbon atoms A represents alkylene containing 2 to 4 carbon atoms, or alkenylene containing 2 or 4 carbon atoms;

$R_6$ represents hydrogen, alkyl containing 1 to 4 carbon atoms, alkoxy containing 1 to 3 carbon atoms, halogen, or hydroxy; and $R_7$ represents hydrogen, alkyl containing 1 to 4 carbon atoms, alkoxy containing 1 to 3 carbon atoms, halogen, or hydroxy;

one of $R_3$ and $R_4$ represents hydrogen and the other represents alkoxy; and y and y′ each represent hydrogen or jointly form a bond, and pharmacologically acceptable acid addition salts thereof.

2. The compound as defined in claim 1 wherein one of $R_3$ and $R_4$ represents hydrogen and the other represents alkoxy containing 1 to 6 carbon atoms.

3. The compound as defined in claim 2 wherein the alkoxy group contains 1 to 4 carbon atoms.

4. The compound as defined in claim 1 wherein the amino group is the chlorophenethylamino group.

5. The compound as defined in claim 1 wherein y and y′ each are hydrogen.

6. The compound as defined in claim 4 which is the 4α-[2-(2-Chlorophenyl)-ethylamino]-3-methyl-8-methoxy-10-methylene-2,9-dioxatricyclo[4,3,1,0³,⁷]decane and its pharmacologically acceptable acid addition salts.

7. The compound as defined in claim 4 which is the 4α-(o-chlorophenethylamino)-3,10-dimethyl-8-methoxy-2,9-dioxatricyclo[4,3,1,0³,⁷]decane and its pharmacologically acceptable acid addition salts.

8. The compound as defined in claim 4 which is the 4β-(o-chlorophenethylamino)-3-methyl-8-methoxy-10-methylene-2,9-dioxatricyclo[4,3,1,0³,⁷]decane and its pharmacologically acceptable acid addition salts.

9. The compound as defined in claim 4 which is the 4β-(o-chlorophenethylamino)-3,10-dimethyl-8-methoxy-2,9-dioxatricyclo[4,3,1,0³,⁷]decane and its pharmacologically acceptable acid addition salts.

10. The compound as defined in claim 1 which is the 4α-(o-methoxyphenethylamino)-3,10-dimethyl-8-methoxy-2,9-dioxatricyclo[4,3,1,0$^{3,7}$]decane and its pharmacologically acceptable acid addition salts.

11. The compound as defined in claim 1 which is the 4α-[2-(3,4-dimethoxyphenyl)ethylamino]-3,10-dimethyl-8-methoxy-2,9-dioxatricyclo[4,3,1,0$^{3,7}$]decane and its pharmacologically acceptable acid addition salts.

12. The compound as defined in claim 1 which is the 4α-(4-fluorophenethylamino)-3,10-dimethyl-8-methoxy-2,9-dioxatricyclo[4,3,1,0$^{3,7}$]decane and its pharmacologically acceptable acid addition salts.

13. The compound as defined in claim 1 which is the 4α-(o-fluorophenethylamino)-3,10-dimethyl-8-methoxy-2,9-dioxatricyclo[4,3,1,0$^{3,7}$]decane and its pharmacologically acceptable acid addition salts.

14. The compound as defined in claim 1 which is the 4α-(o-bromophenethylamino)-3,10-dimethyl-8-methoxy-2,9-dioxatricyclo[4,3,1,0$^{3,7}$]decane and its pharmacologically acceptable acid addition salts.

15. The compound as defined in claim 4 which is the 4α-[N-(o-chlorophenethyl)methylamino]-3,10-dimethyl-8-methoxy-2,9-dioxatricyclo[4,3,1,0$^{3,7}$]decane and its pharmacologically acceptable acid addition salts.

16. The compound as defined in claim 4 which is the 4α-[N-(o-chlorophenethyl)allylamino]-3,10-dimethyl-8-methoxy-2,9-dioxatricyclo[4,3,1,0$^{3,7}$]decane and its pharmacologically acceptable acid addition salts.

17. The compound as defined in claim 1 which is the 4α-(3-phenylpropylamino)-3,10-dimethyl-8-methoxy-2,9-dioxatricyclo[4,3,1,0$^{3,7}$]decane and its pharmacologically acceptable acid addition salts.

18. The compound as defined in claim 1 which is the 4αa-(4-phenylbutylamino)-3,10-dimethyl-8-methoxy-2,9-dioxatricyclo[4,3,1,0$^{3,7}$]decane and its pharmacologically acceptable acid addition salts.

19. The compound as defined in claim 4 which is the 4α-[3-(2-chlorophenyl)-propylamino]-3,10-dimethyl-8-methoxy-2,9-dioxatricyclo[4,3,1,0$^{3,7}$]decane and its pharmacologically acceptable acid addition salts.

20. The compound as defined in claim 1 which is the 4α-(cinnamylamino)-3,10-dimethyl-8-methoxy-2,9-dioxatricyclo[4,3,1,0$^{3,7}$]decane and its pharmacologically acceptable acid addition salts.

21. The compound as defined in claim 1 wherein the acid in the pharmacologically acceptable acid addition salt is hydrochloric acid, maleic acid or tartaric acid.

22. A pharmaceutical composition for inhibiting pain comprising an analgesically active amount of at least one compound as defined by claim 1.

23. A pharmaceutical composition for inhibiting pain comprising an analgesically active amount of at least one compound as defined by claim 7.

24. A method of treatment of pains in larger mammals which comprises the step of administering to a larger mammal an analgesically active amount of a compound as defined in claim 1.

25. A method of treatment of pains in larger mammals which comprises the step of administering to a larger mammal an analgesically active amount of a compound as defined in claim 7.

* * * * *